United States Patent [19]

Bickel et al.

[11] 4,302,448

[45] Nov. 24, 1981

[54] SECRETIN PREPARATIONS WITH INTENSIFIED AND PROTRACTED ACTION, PROCESS FOR THEIR MANUFACTURE, THEIR USE AS WELL AS DIHYDROXYBENZOYL-L-TYROSINE

[75] Inventors: Martin Bickel; Rolf Geiger, both of Frankfurt am Main; Richard Leeb, Kelkheim; Walter Petri, Niedernhausen, all of Fed. Rep. of Germany

[73] Assignee: Hoechst Aktiengesellschaft, Frankfurt am Main, Fed. Rep. of Germany

[21] Appl. No.: 158,595

[22] Filed: Jun. 11, 1980

[30] Foreign Application Priority Data

Jun. 13, 1979 [DE] Fed. Rep. of Germany ....... 2923878
Apr. 3, 1980 [DE] Fed. Rep. of Germany ....... 3013105

[51] Int. Cl.$^3$ ............................................. A61K 37/00
[52] U.S. Cl. .................................................... 424/177
[58] Field of Search .................. 260/112.5 R; 424/177

[56] References Cited

U.S. PATENT DOCUMENTS 3,740,385 6/1973 Ondetti ................................ 424/177
4,098,779 7/1978 König et al. ................. 260/112.5 R

FOREIGN PATENT DOCUMENTS 7203099 9/1972 France ................................ 424/177
109489 8/1964 Netherlands ........................ 424/177

OTHER PUBLICATIONS

Demling et al., Chem. Abstr., vol. 80, (1974), 34056q.
Research Disclosure, 169, 4–6, (1978), #16909, "Stable Secretin Preparation".

Primary Examiner—Delbert R. Phillips
Attorney, Agent, or Firm—Curtis, Morris & Safford

[57] ABSTRACT

What are disclosed are secretin preparations with an intensified and protracted action, especially subcutaneously and rectally administrable preparations containing phenolic depot bodies. A process for the manufacture of the preparations and their use as well as phenolic depot bodies and the manufacture thereof are described.

9 Claims, 1 Drawing Figure

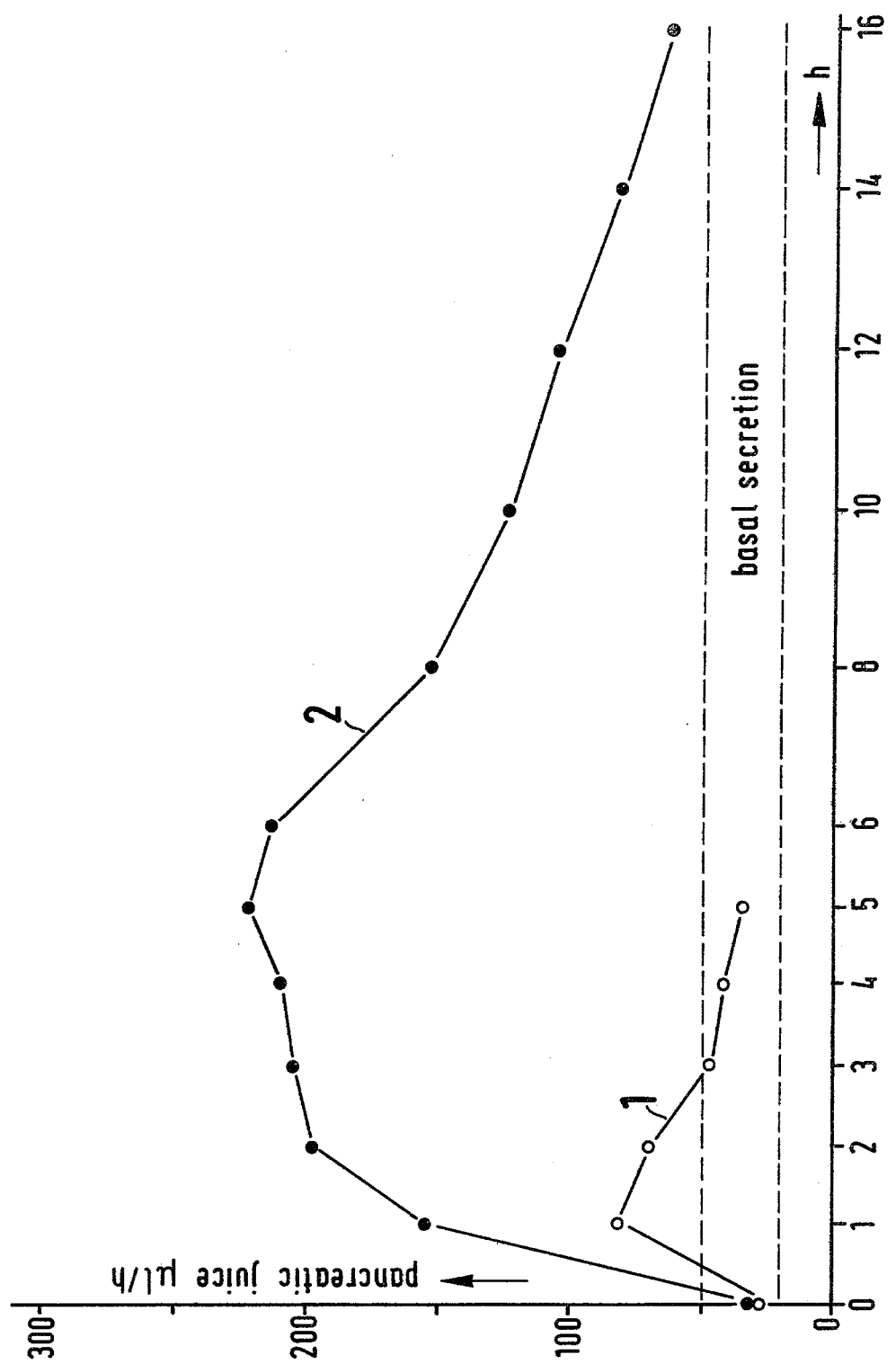

SECRETIN PREPARATIONS WITH INTENSIFIED AND PROTRACTED ACTION, PROCESS FOR THEIR MANUFACTURE, THEIR USE AS WELL AS DIHYDROXYBENZOYL-L-TYROSINE

The invention relates to secretin preparations having an intensified and protracted action, especially secretin preparations which may be administered subcutaneously and rectally.

Attempts have been made again and again to protract the short action of the hormone secretin by suitable injection compositions. So far, only one preparation showing this quality has been described, namely a composition of secretin, polyphloretin phosphate (PPP) and gelatin derivatives (German Pat. No. 2,104,344).

The effect of PPP is attributed to its hyaluronidase-inhibiting action and to its capability of binding the basic secretin. The effect of the gelatin derivative is seen in an additional delay of the secretin absorption, with adduct formation also being observed. With these preparations there is the risk of undesirable reactions due to a deposit of PPP in the tissue.

Many medicaments may be incorporated in suppositories and administered rectally. They are sufficiently well absorbed in this form. For peptides, suppositories or rectal capsules do not represent a suitable form of administration, since in this case the rate of absorption is too low for normal practice. For example, if secretin is administered by this route, the biological effect which is measured via pancreatic juice secretion is only about 1% of the effect obtained with subcutaneous injection.

Surprisingly, it has now been found that phenol bodies which do not show any hyaluronidase inhibition and are of low molecular weight (when compared with PPP) intensify and prolong the secretin action of secretin injection preparations in vivo.

It has also been found that the available amount of secretin may be considerably increased in the case of rectal administration in suppositories, if certain phenolic compounds are added to the suppository mass. At the same time said compounds prolong the action of the secretin, as this has been observed also for secretin injection preparations.

Thus, the present invention provides a secretin preparation with an intensified and protracted action, which contains a phenolic depot body showing a molecular weight of up to about 2,000 and having one or several benzene nuclei with at least one phenolic OH group, wherein the nucleus carrying the phenolic group may also be condensed to a hydroxynaphthyl, a hydroxyindole or a hydroxyquinoline radical.

In the above and the following passages the term secretin includes natural and synthetic secretin, especially in the form of physiologically acceptable salts, for example the hydrochloride, acetate or citrate. Besides, by "phenolic depot bodies" there are to be understood in the above and the following passages the phenolic compounds to be used in accordance with the invention. The invention relates especially to secretin injection preparations and rectally administrable secretin preparations.

By administering the phenolic depot bodies as defined above, the risk of a deposit of higher molecular compounds in the tissue which might lead to undesirable reactions, is avoided. The protracted and intensified action of secretin becomes already clearly evident with phenol itself. Yet compounds with several phenolic groups and benzene nuclei show a stronger effect. By varied substitution the degree of efficacy is modified without a recognizable pattern. A marked prolongation of efficacy is always linked with the presence of at least one free phenolic group in the molecule. The effects in subcutaneous and rectal application are not always parallel. Thus, for example, a typical compound, namely 3,5-dihydroxy-benzoyl-L-tyrosine, leads to a greater increase in efficacy when applied rectally than with subcutaneous application.

The depot bodies used according to the invention preferably contain from 1 to 12 benzene nuclei, with one or several of these nuclei containing up to 3 phenolic hydroxy groups. It is not required that all phenyl radicals of a molecule carry phenolic groups. The phenyl radicals may be condensed to hydroxynaphthyl, hydroxyindole or hydroxyquinoline radicals.

Besides, the phenyl radicals present in the molecule may be condensed and/or bound to one another directly and/or via bridge members. Bridge members of this kind are for example alkyl, ether, thioether, carbonamides, sulfoxides, sulfone, urethane, disulfide, sulfonamide, cetone, phosphoric acid ester and alkylphosphine oxide. The bridge members show 8 atoms at a maximum in linear order, or in the case of alkyl the alkyl radicals have up to 8 carbon atoms. The phenyl radicals—including those which carry OH groups—and the bridge members may be further substituted by alkyl, cycloalkyl, hydroxyalkyl, halogen, nitro, carboxy, carbonamido, sulfonic acid, sulfonamide, alkyl sulfoxide, alkyl sulfone, phosphoric acid ester, phosphoric acid, dialkylphosphine oxide and/or alkylphosphonic acid. If these substituents include alkyl groups, said alkyl groups have up to 8 carbon atoms. If phenylcarboxylic acid radicals are present in the depot body, they may be bound to polyamides like acid amides.

A decisive factor for the efficacy of the depot bodies employed is not to be seen in the substituents optionally present, but in the presence of one or several phenolic OH groups.

An additional prolongation of the secretin effect in the preparations that may be administered subcutaneously is ensured by the fact that the preparation contains, besides a phenolic physiologically acceptable depot body, a gelatin derivative which is prepared either 1. by a reaction of collagen degradation products of a molecular weight of from 2000 to 20,000 with an amount of diisocyanate smaller than that corresponding to the number of the amino and guanidino groups present in the degraded collagen, at 0° to 100° C. in the neutral or slightly alkaline range and subsequent adjustment of the cross-linked product to a pH value of 7 and to isotonicity by way of sodium chloride, or
2. by a further degradation of the cross-linked product obtained according to step (1) in aqueous solution at 60° to 150° C. up to a molecular weight of from 10,000 to 100,000 and subsequent adjustment to pH 7 and isotonicity according to (1) above.

Secretin preparations for subcutaneous application which contained the depot bodies specified in the following Table were tested in animal experiments. In the experimental procedure chosen, 5 to 8 male rats weighing 300 to 500 g each are administered subcutaneously 5 CU/kg of secretin (CU means clinical unit) and 10 mg of the depot body to be tested each in aqueous solution or suspension. As solubilizers there are used N'-methyl pyrrolidone, dimethyl sulfoxide, dimethyl formamide, tetrahydrofurfuryl alcohol-polyethylene glycol ether, polyethylene glycol, 1,3-butylene-glycol or 1,2-propylene glycol, which by themselves do not involve any intensification of the secretin effect.

The animals remain without food for 18 hours prior to the test, but they are given water ad libitum. Under urethane anaesthesia (5 ml/kg i.m. of 25% urethane) the abdomen is opened by median section after tracheotomy, and the pylorus is ligated. The ductus choledochus is tied off in its proximal part near the porta hepatis, and the bile is led into the duodenum via a polyethylene tube of a diameter of 0.05 mm. A cannula or catheter is inserted into the distal part of the bile duct, into which the numerous pancreatic ducts open, immediately before it opens into the duodenum, and the volume of the secretion running off is measured in 60 minute intervals. Following a preliminary run of 60 minutes the preparations are administered.

In the following Table, column 1 shows the depot body, column 2 the method of preparation. L means the compound known from literature and characterized by the melting point, optionally UV, IR or NMR. A to C relate to the preparation according to Example 1, process A to C. These compounds were characterized by ultimate analysis. The third column indicates the percentage by which the pancreatic secretion is above the basal secretion after 5 hours (calculated on the control=100%). This value is a measure for the depot effect of the depot body tested. Column 4 indicates the intensification of the secretin effect, with the total pancreatic juice secretion having been given over 5 hours as compared with the control (0.9% of NaCl)=1.

TABLE

Pancreatic juice secretion of the rat after subcutan. administration of 5 CU/kg of secretin with different depot bodies (10 mg/animal)

| 1 Depot body | 2 Preparation | 3 Δ% vs. control | 4 Rel. Intensity of effect over 5 hours |
| --- | --- | --- | --- |
| Phenol | L | 51 | 8 |
| Resorcinol | L | 55 | 6.1 |
| Pyrogallol | L | 41 | 5.1 |
| Phloroglucine | L | 15 | 6.6 |
| 2-Hydroxyacetophenone | L | 38 | 7.6 |
| 3-Hydroxy-acetophene | L | 54 | 9.0 |
| 4-Hydroxyacetophenone | L | 43 | 8.1 |
| 2,4-Dihydroxy-acetophenone | L | 70 | 6.1 |
| 2-Hydroxy-benzophenone | L | 74 | 7.2 |
| 3-Hydroxy-benzophenone | L | 79 | 8.0 |
| 4-Hydroxybenzophenone | L | 70 | 6.7 |
| 2,4-Dihydroxy-benzophenone | L | 163 | 9.1 |
| 2,2'-4,4'-Tetrahydroxybenzophenone | L | 58 | 4.8 |
| 2,3,4-Trihydroxy-benzophenone | L | 109 | 9.1 |
| Phloretin | L | 180 | 8.2 |
| 4,4'-Dihydroxy-diphenyl sulfone | L | 74 | 6.2 |
| 4-Hydroxyphenylmethyl sulfoxide | L | 96 | 12.3 |
| 4-Hydroxyphenylmethyl sulfone | L | 8 | 6.0 |
| 4-Hydroxybenzene-sulfonic acid-Na | L | 18 | 2.7 |
| Phloretin monophosphate | L | 65 | 7.7 |
| Bis-phloretin phosphate | L | 56 | 2.5 |
| Phloretin-3,5-dimethylphenyl phosphate | L | 68 | 3.7 |
| 3,5-Dihydroxyphenylcarbonyl-ethylphenyl-3,5-dimethyl phosphate | L | 62 | 3.4 |
| 2-Hydroxy-quinoline-4-carboxylic acid | L | 5 | 5.0 |
| 8-Hydroxyquinoline | L | 37 | 4.7 |
| 2-Hydroxy-benzoic acid | L | 6 | 4.5 |
| 2-Hydroxy-benzoic acid amide | L | 51 | 8.0 |
| 3-Hydroxybenzoic acid | L | 47 | 4.0 |
| 4-Hydroxybenzoic acid | L | 38 | 3.8 |
| 4-Hydroxy-benzoic acid-methyl-ester | L | 15 | 5.3 |
| 4-Hydroxy-benzyl alcohol | L | 12 | 1.3 |
| 3,5-Dihydroxybenzoic acid-3-hydroxy-anilide | B | 49 | 6.2 |
| 2,4-Dihydroxybenzoic acid | L | 28 | 7.1 |
| 3,4,5-Trihydroxybenzoic acid | L | 28 | 5.0 |
| 3,5-Dihydroxybenzoic acid | L | 25 | 6.6 |
| 3,5-Dihydroxybenzoic acid amide | L | 34 | 6.2 |
| 2,4-Dihydroxybenzoic acid-benzylamide | L | 64 | 6.8 |
| Bis-(2,4-dihydroxybenzoyl-)-diaminoethane | B | 69 | 6.5 |
| Bis-(3,5-dihydroxybenzoyl)-diaminoethane | A | 79 | 6.1 |
| Bis-(2-hydroxybenzoyl)-diaminoethane | A | 72 | 5.9 |
| Bis-(2,4-dihydroxybenzoyl)-1,4-diaminobutane | B | 83 | 6.7 |
| Bis-(3,5-dihydroxybenzoyl)-1,4-diaminobutane | A,B | 85 | 7.4 |
| Tris-(2-hydroxybenzoyl)-diethylene-triamine | B | 62 | 8.1 |
| Tris-(3-hydroxybenzoyl)-diethylene-triamine | A | 71 | 8.0 |
| Tris-(4-hydroxybenzoyl)-diethylene-triamine | B | 68 | 7.8 |
| Tris-(3,5-dihydroxybenzoyl-diethylene-triamine | A | 79 | 8.6 |
| Tetra-(2-hydroxybenzoyl)-triethylene-tetramine | A | 91 | 9.0 |
| Tetra-(3-hydroxybenzoyl-)triethylene-tetramine | A | 95 | 9.1 |
| Tetra-(3,5-dihydroxybenzoyl)-triethylene-tetramine | A | 101 | 9.7 |
| Tetra-(2,6-dihydroxybenzoyl)-triethylene-tetramine | B | 78 | 8.1 |
| 2,8-Dihydroxy-3-naphthoyl-diethanolamine | B | 77 | 9.1 |
| Tris-(2,8-dihydroxy-3-naphthoyl)-diethylene-triamine | B | 94 | 9.4 |
| 1-Hydroxy-2-naphthoic acid-diethanolamide | A,B | 79 | 8.1 |
| 1-Hydroxy-2-naphthoic acid-ethanolamide | A,B | 74 | 8.0 |
| 2-Hydroxy-5-chloro-benzoic acid-diethanolamide | A | 77 | 7.3 |
| Bis-(3,5-dihydroxybenzoyl)-cystamine | A,B | 79 | 8.0 |
| 3-(2-Hydroxybenzoylamino)-benzene-sulfonamide | A | 81 | 8.1 |
| Tetra-(3,5-dihydroxybenzoyl-L-tyrosyl)-triethylene-tetramine | A | 98 | 9.5 |
| 3,5-Dihydroxybenzoyl-aminomethyl-phosphonic acid | A | 75 | 8.9 |
| 2,4-Dihydroxybenzoyl-aminomethyl-dimethylphosphine oxide | B | 79 | 8.6 |
| 2,4-Dihydroxybenzoyl-L-tyrosine-methyl ester | B | 70 | 7.8 |
| Nα,Nε-Bis(3,5-dihydroxybenzoyl-L-tyrosyl)-L-lysine-diethanol-amide | C | 86 | 8.8 |
| Benzyloxycarbonyl-L-tyrosine | L | 7 | 5.9 |
| 3,5-Dihydroxybenzoyl-L-tyrosine | B | 76 | 9.2 |
| 2,4-Dihydroxybenzoyl-L-tyrosine | B | 84 | 10.5 |
| 2,4-Dihydroxybenzoyl-L-tyrosine-n-butylamide | C | 87 | 8.7 |
| 3,5-Dihydroxybenzoyl-L-tyrosine-di-ethanolamide | C | 76 | 7.6 |
| 2,4-Dihydroxybenzoyl-L-tyrosine-di-ethanolamide | C | 47 | 8.7 |
| Bis-(benzyloxycarbonyl-L-tyrosine)-diaminoethane | C | 44 | 5.5 |
| Bis-(3,5-dihydroxybenzoyl-L-tyrosine)-diaminoethane | C | 58 | 7.0 |
| Bis-(2-carboxybenzoyl-L-tyrosine)- | C | 48 | 6.3 |

TABLE-continued

Pancreatic juice secretion of the rat after subcutan. administration of 5 CU/kg of secretin with different depot bodies (10 mg/animal)

| 1 Depot body | 2 Preparation | 3 Δ% vs. control | 4 Rel. Intensity of effect over 5 hours |
|---|---|---|---|
| diaminoethane | | | |
| Bis-(2,4-dihydroxybenzoyl-L-tyrosine)-diaminoethane | C | 82 | 6.0 |
| Bis-(3-benzoylpropionyl-L-tyrosine)-diaminoethane | C | 60 | 3.7 |
| Benzyloxycarbonyl-L-tyrosyl-L-tyrosine | L | 62 | 7.5 |
| Nα,Nε-Bis-(benzyloxycarbonyl-L-tyrosyl)-L-lysine | C | 48 | 7.0 |
| Nα,Nε-Bis-(benzyloxycarbonyl-L-tyrosyl)-D-lysine | C | 13 | 1.5 |
| Nα,Nε-Bis-(benzyloxycarbonyl-L-tyrosyl)-L-lysine-methyl ester | C | 93 | 8.2 |
| Nα,Nε-Bis-(benzyloxycarbonyl-L-tyrosyl)-L-lysine-amide | C | 90 | 8.4 |

As may be seen from the Tables, all phenolic depot bodies tested have a protracting and intensifying influence on the secretin.

The depot bodies which may be employed according to the invention are either compounds known from the literature or those which are prepared, for example, in accordance with the methods described in the experimental part. It is a great advantage that even low molecular weight compounds of simple structure which may easily be obtained are suitable depot bodies.

The fact that these phenolic depot bodies are not only present in admixture with secretin, but also form addition products with the latter, may easily be seen from the drastic reduction of the molecular extinction of the phenols in the proximity of 280 nm by up to 50%, while adding increasing amounts of secretin.

However, since the said adduct formation is reversible and subject to the law of mass action, it is advantageous to use a large molar excess of depot bodies. For subcutaneous administration in humans, from 10 to 100 mg of a depot body in 1 to 2 ml of solution or suspension are used per 80 to 1000 clinical units (CU; 1 mg of secretin=4000 CU; according to Gut 19 (1978, page 355), 1 mg of secretin is reported to have a biological effect corresponding to 5000 CU). If a gelatin derivative is added to improve the effect, its concentration is from 30 to 100 mg/ml. Also the gelatin derivatives optionally present in the secretin reduce the UV extinction of the phenols and are thus present in a complex bond. For preparing the adducts and mixtures it is sufficient to bring the components into contact with one another for a short time in a solution. The adduct formation takes place rapidly.

As phenolic depot bodies for the rectally administrable secretin preparations, those specified in the Table may also be used.

It is a great advantage also for this type of preparation that already even low molecular weight compounds of simple structure which are easily accessible are suitable to increase the available amount of secretin from suppositories or rectal capsules in a way that a rectal administration of secretin becomes possible or useful for the first time. The reversible adduct formation mentioned before also takes place, and it is equally advantageous to use a large molar excess of depot bodies.

The intensified effect of secretin in the form of rectally administrable preparations due to the depot bodies used according to the invention becomes evident from the drawing. In a test carried out on 8 rats each weighing 0.5 kg, 100 μg of secretin in a suppository of a weight of 73 mg cause the production of 92 μl of pancreatic juice (curve 1). With the addition of 25 mg of 3,5-dihydroxybenzoyl-L-tyrosine the volume of pancreatic juice rose to 1778 μl (curve 2). This corresponds to an increase of the effect to about 20 times its original value. Besides, a protracted action can also be observed. In the present case the secretin dose has been chosen very high in order to obtain a measurable volume also without additive.

With a non-maximum stimulation in the normal dose range (about half the dose), the increase of the effect is about 50-fold.

For the treatment of humans, from about 0.1 to 2 mg of secretin are required per suppository (=400 to 8000 clinical units CU; 1 mg of secretin=4000 CU; according to Gut 19 (1978), page 355, 1 mg of secretin is stated to have a biological effect corresponding to 5000 CU). The minimum amount of depot bodies is about 50 mg. The maximum amount is determined by the processibility. For a suppository of a weight of about 2 g it is up to 1 to 1.5 g.

Another subject of the invention is a process for the manufacture of a secretin preparation having a protracted and intensified action.

A subcutaneously administrable preparation of the invention is preferably obtained by dissolving secretin hydrochloride prepared according to U.S. Pat. No. 4,098,779 (corresponding to German Offenlegungsschrift No. 2,615,229) in water or in the aqueous solution of one of the above-specified gelatin derivatives and combining the resulting solution with the solution of the depot body in water. In this process the pH value is in the range of from 7 to 8.5. It is adjusted to 7.0 to 7.8 with a physiologically acceptable acid, whereupon the solution is lyophilized.

Some depot bodies are sparingly soluble and are present under the above conditions in a suspension. In this case an amorphous or crystalline suspension is prepared by precipitation of the phenols dissolved at pH 10 and adjustment of the pH to the range between 7.0 and 7.4, which suspension may be stabilized by the presence of a gelatin derivative as defined above. This suspension is combined with the aqueous solution of secretin, or lyophilized secretin is dissolved in this aqueous suspension. Already after a short time the secretin is fully adsorbed on the depot body. This secretin-containing suspension should be injected within one week.

Furthermore, it is also possible to dissolve the phenolic depot bodies in water containing up to 30% of a solubilizer. Suitable solubilizers are 1,2-propylene glycol, 1,3-butylene glycol, polyethylene glycol, tetrahydrofurfuryl alcohol-polyethylene glycol ether, dimethyl sulfoxide, N-methyl pyrrolidone or dimethyl formamide. In this case the solution of the depot carrier is preferably prepared without secretin, and said solution which is not lyophilized is filled into ampules of preferably 1 to 2 ml. In a second ampule the secretin is present in a lyophilized state. Immediately prior to application the secretin is dissolved in the solution of the depot carrier, whereupon the adduct is formed. A gelatin derivative may optionally be added to the secretin or the depot body or both.

The process for the manufacture of rectally administrable secretin preparations with protracted and intensified action comprises preparing suppositories or rectal capsules from a mixture of a generally common carrier, secretin and a phenolic depot body as characterized above.

As suppository mass, known compounds, for example partial glycerides, i.e. mixtures of mono- and diesters of glycerol with higher fatty acids, furthermore fatty acid-1,2-propylene-glycol esters, and moreover polyethylene glycols with a solidification range of from about 30° to 50° C. are used. The secretin incorporated into masses of this kind or into oil, together with the phenols to be used according to the invention, may also be filled into commercial rectal capsules.

The suppositories are manufactured by homogenizing the mixture of carrier, secretin and a phenol to be used according to the invention in the melt and subsequently filling it into suppository molds, while still in the liquid state, in which molds said mixture is allowed to solidify. Semisolid or oily suspensions are filled into rectal capsules. The weight of a suppository is from about 1 to 3 g.

In a similar manner it is also possible to manufacture suppositories comprising glycerol and gelatin.

Suppository masses such as fatty acid-1,2-propylene glycol ester are mixed together with secretin and a depot body to be used according to the invention and molded into granules without melting. The suppositories or rectal capsules of the invention are used for treating and preventing hemorrhages of the intestinal tract and for the treatment of ulcers. They represent the first secretin preparation not to be administered by injection.

The invention relates further to the phenolic compounds specified in the Table which have not yet been described in literature, which may be prepared according to the processes indicated above and are used as depot bodies for the secretin preparations of the invention. A special subject of this invention is 3,5-dihydroxybenzoyl-L-tyrosine.

Phenolic depot bodies with carbonamide groups are synthesized according to common methods for the preparation of carbonamide compounds, if they have not been known from literature.

Particularly suitable and easily accessible depot bodies, as they are specified in the Table, may be prepared, for example, from hydroxyl group-carrying carboxylic acids and amines. Amine components may also be amines optionally carrying hydroxyl groups, amino acid esters, peptide esters or amino acid- or peptide amides. If the amine components contain carboxylic acid groups, the latter are advantageously prepared from the corresponding esters, in most cases methyl esters, by saponification. By the action of ammonia or amines on these esters amides are formed. Further functional groups have to be blocked temporarily, if necessary, by protective groups such as are common in peptide chemistry.

Furthermore, the phenolic OH groups may also be protected, for example, by acetylation, during the amide synthesis. The protective groups are split off from the reaction product in known manner by a treatment with alkali, ammonia or amines. It is also possible, however, to prepare the amide bond without previous protection of the OH groups if the condensation is carried out by way of carbodiimide in the presence of an additive such as 1-hydroxybenzotriazole (Chem. Ber. 103, (1970) pages 788 to 798).

2-Carboxy-carbonamide groups are prepared from the inner anhydrides.

The phenolic depot bodies to be used in accordance with the invention may be present in part as salts, for example alkali metal or alkaline earth metal salts, or as salts with organic bases, for example trishydroxymethylaminomethane. These salts are obtained, for example, by dissolving or suspending the corresponding phenolic compound in water and adding a base, while stirring, until a pH of from 7.0 to 7.5 is reached and maintained.

The secretin preparations of the invention are used for treating and preventing hemorrhages of the intestinal tract and for the treatment of ulcers, said preparations being administered by injection or rectally.

In the following Examples, general directions which are easy to carry out have been indicated for preparing the depot bodies and depot preparations, however, without restricting the invention.

EXAMPLE 1

Components such as alkylamine, esters, tert. amine or alkylamide mentioned in this Example contain up to 8 carbon atoms.

A. 1 Mol of an acetoxy-benzoic acid is boiled in 5 times the amount (g/v) of thionyl chloride for a period of from 30 minutes to 1 hour. The excess thionyl chloride is distilled off, then the batch is redistilled with toluene, and the residue is dissolved in toluene, tetrahydrofuran, dimethyl acetamide or other substances and combined with 2 moles of amine component (alkylamine, dialkylamine, morpholine, tyrosine ester or tyrosine alkylamide, lysine ester or lysine alkylamide, aminoalkyl-phosphonic acid, aminoalkyl-dialkyl-phosphine oxide, aminobenzene sulfonamide and others) or with 1 mol of amine component and 1 mol of a tertiary amine, whereupon the mixture is allowed to react for 1 to 2 hours at room temperature, with stirring. For work-up, the reaction mixture is poured into water, the precipitate is filtered off and purified by recrystallization from methanol or other substances. If the compound is too easily soluble in water, the solvent is distilled off, and the residue is digested with a small amount of water or ethanol. The product is purified by recrystallization from isopropanol, ethyl acetate, or similar substances.

In order to split the acetoxy groups and esters, if any, the product is saponified with 1.5 mols of 2 N NaOH per cleavable group in methanol or methanol/dioxan/water (about 3:3:1). It is neutralized after about 1 hour with HCl, the solvent is distilled off, thereafter the product is taken up (optionally suspension) in water and acidified with HCl. The precipitate is filtered off and washed with water. In the case of easily water-soluble compounds, the solution of the compounds is diluted directly following the saponification with methanol/water (1:1), filtered via a strongly acid ion exchanger and evaporated to dryness. The residue is recrystallized from a suitable solvent such as isopropanol, ethyl acetate, or similar substances.

B. 1 Mol of a hydroxy-benzoic acid and 1 mol of an amine component according to Example 1 A are dissolved in dimethyl formamide. There are added 1 mol of 1-hydroxy-benzotriazole and 1 mol of dicyclohexyl carbodiimide, after 4 hours the solution is filtered off from the precipitated dicyclohexyl urea, thereafter a crude product is precipitated with petroleum ether which may be purified by digesting with methanol or by recrystallization from methanol or isopropanol. Esters are optionally saponified according to Example 1 A.

3,5-Dihydroxybenzoyl-L-tyrosine a. 3,5-Dihydroxybenzoyl-L-tyrosine methyl ester 231.2 g of 3,5-dihydroxybenzoic acid are dissolved in 4 l of dimethyl formamide. 313 g of L-tyrosine-methyl ester hydrochloride, 202 g of 1-hydroxybenzotriazole and 346 ml of N-ethyl morpholine and subsequently 297 g of dicyclohexyl carbodiimide are added. The mixture is stirred over night at room temperature, and the precipitated dicyclohexyl urea is filtered off. The solvent is distilled off in vacuo, the residue is taken up in 4 l of ethyl acetate, the ethyl acetate solution is washed 4 times each with saturated sodium bicarbonate solution, 3 times with 400 ml portions of a solution of 5% $KHSO_4$ and 10% $K_2SO_4$ and twice with 200 ml portions of water, dried over sodium sulfate and subsequently brought to dryness. Yield: 360 g of resin.

b. 3,5-Dihydroxybenzoyl-L-tyrosine

The resin as obtained above is dissolved in about 1.4 l of 2 N NaOH, and the solution is adjusted to pH 12.5 with 6 N NaOH. The reaction mixture is saponified under a nitrogen atmosphere and with pH control, while adding 2 N NaOH and maintaining a constant pH of 12.5 (period: about 15 hours). The alkaline solution is extracted 4 times with 500 ml portions of n-butanol. The aqueous phase is neutralized with 6 N HCl, treated for 10 minutes with active charcoal (50 g), filtered and further acidified, as long as an oil separates. Said oil is taken up in 1 l of n-butanol, the aqueous phase being extracted again twice with 300 ml portions of n-butanol. The combined butanol phases are washed twice with 100 ml portions of saturated sodium chloride solution and once with 150 ml of water, dried over sodium sulfate, filtered and freed from the solvent in vacuo. The remaining oil is dissolved in 600 ml of acetone. The solution is filtered and introduced dropwise into 8 l of chloroform, while stirring vigorously. The precipitate is collected, washed with chloroform and dried in vacuo. Yield: 255 g of a slightly hygroscopic powder. The compound and the dicyclohexylamine salt thereof melt with decomposition.

$C_{16}H_{15}NO_6$, 0.5 $H_2O$: 326.3; calc. C 58.89 H 4.94 N 4.29 found C 58.9 H 5.2 N 4.2

C. 1 Mol of a hydroxybenzoyl-tyrosine or -tyrosyl-tyrosine prepared according to Examples 1 A or 1 B is reacted according to Example 1 B with one of the above-mentioned amine components. The work-up and the purification are carried out as under 1 B. Carboxylic acid esters may be saponified according to Example 1 B, the carboxylic acids obtained may be reacted once again with an amine component according to Example 1 B.

EXAMPLE 2

A suspension of 0.5 to 1 g of secretin hydrochloride and 250 g of 3,5-dihydroxybenzoyl-L-tyrosine is homogenized at 40° to 60° C. in 480 g of suppository mass consisting of a partial glyceride or polyethylene glycol with a solidification point of from 30° to 50° C. in each case, and the product obtained is filled into suppository molds, while still in the liquid or semiliquid state. The weight of a suppository is about 2 g.

EXAMPLE 3

Operations are the same as those described under Example 2, save for using only 0.05 g of secretin hydrochloride.

EXAMPLE 4

The process is carried out according to Example 2 or 3, while using 250 g of the sodium salt of 3,5-dihydroxybenzoyl-L-tyrosine.

EXAMPLE 5

The process is carried out as has been described in Example 2, 3 or 4, save for using 1 g of secretin citrate and 1000 g of suppository mass.

EXAMPLE 6

A mixture of 0.5 g of secretin citrate, 200 g of 3,5-dihydroxybenzoyl-L-tyrosine or one of the physiologically acceptable salts thereof and 500 g of a partially hydrogenated vegetable oil, for example sesame oil, soybean oil, palm oil or colza oil, is homogenized, and 2.0 g each are filled into rectal capsules.

EXAMPLE 7

1 Gram of secretin hydrochloride is incorporated into a mixture of 250 g of the sodium salt of 3,5-dihydroxybenzoyl-L-tyrosine and 500 g of fatty acid-1,2-propylene glycol ester, the resulting product is granulated and molded into suppository molds.

EXAMPLE 8

At about 50° C., 0.5 g of secretin hydrochloride is dissolved, while stirring, in a solution of 110 g of gelatin and 90 g of glycerol in 300 ml of water. The resulting solution is then mixed with 200 g of trishydroxymethyl aminomethane salt of 3,5-dihydroxybenzoyl-L-tyrosine, then the mixture is filled into suppository molds and is allowed to cool rapidly.

EXAMPLE 9

Operations are as described in Examples 2 to 8, save for using another phenolic depot body with a corresponding amount by weight.

EXAMPLE 10

A solution is prepared, for example, of

A. 30 g of bis-phloretin-sodium phosphate (obtained according to C.A. 78, 147 558 g) in 300 ml of water
B. 80 g of gelatin derivative in 500 ml of water
C. 1 million CU of secretin and 2 g of NaCl in 100 ml of water.

The solution A to C are purified and made up of 1.0 liter with water. They are filtered under sterile conditions, filled under aseptic conditions into ampules of 1 ml each and lyophilized.

EXAMPLE 11

The process is carried out as has been described in Example 10. However, only the two solutions A and B are combined and made up to 1 liter, whereupon the solution is filled into ampules of 1 ml and lyophilized. Solution C contains, besides 1 million CU of secretin, 20 g of glycine and 2 g of gelatin derivative and is separately filled in the same manner into ampules of 1000 CU each and lyophilized.

Prior to being used, the depot body is dissolved in 1 ml of water. The lyophilized secretin is taken up in this solution and injected.

EXAMPLE 12

30 Grams of 4-hydroxyphenyl-methylsulfoxide are dissolved in a mixture of 200 ml of 1,2-propylene glycol and 200 ml of water, and the resulting solution is combined with the solution of 80 g of gelatin derivative in 500 ml of water. The mixture is made up with water to 1 liter, filtered under sterile conditions and filled into ampules of 1 ml each.

This solution is used to absorb the secretin prepared according to Example 11. Upon dissolution of the ampule contents, injections may be made immediately.

EXAMPLE 13

30 Grams of phloretin are dissolved with the aid of 2 N NaOH in 300 ml of water, and after filtration of the solution the compound is precipitated in a finely divided form by adjusting the pH to 7.0 to 7.4 with diluted HCl. By stirring for a shorter or prolonged period, the particle size may be modified and for example brought to an appropriate value (e.g. 15 to 35µ). The substance is then combined with the sterile solution of 80 g of gelatin derivative in 500 ml of water, the total volume is made up to 1 liter and filled into ampules of 1 ml each.

Prior to being used, the suspended depot body is homogeneously distributed in the solution by slight agitation. Thereupon a secretin prepared according to Example 11 is dissolved in the aqueous suspension, the solution is agitated for a short time and injected.

EXAMPLE 14

30 Grams of 2,4-dihydroxybenzoyl tyrosine are dissolved in a manner analogous to that of Example 12 in 200 ml of propylene glycol and 800 ml of water, filtered under sterile conditions and filled into ampules of 1 ml each. In order to be used, the secretin filled into ampules according to Example 11 is taken up in this solution and injected.

EXAMPLE 15

30 Grams of 2,4-dihydroxybenzoyl-L-tyrosine are dissolved in 800 ml of water, while adding 1 N NaOH up to about pH 8.5. The solution is then adjusted to pH 7.4 with 1 N HCl, made up with water to 1.0 l, filtered, filled into ampules of 1 ml each and lyophilized. In order to be used, the ampule contents are taken up in 1 ml of water, and the secretin filled into ampules according to Example 11 is dissolved therein.

EXAMPLE 16

Operations are the same as in Examples 10 to 13, save for using only 15 g of a phenolic depot body and optionally 40 g of a gelatin derivative.

EXAMPLE 17

Operations are the same as in Example 10 to 13, save for using 60 g of a depot body and optionally 80 g of a gelatin derivative.

EXAMPLE 18

Use is made of one of the phenols specified in the Table, the compound being employed in a manner analogous to that of Examples 10 to 15, depending on its solubility.

What is claimed is:

1. A secretin preparation having an intensified and protracted action, said preparation comprising secretin and a phenolic depot body having a molecular weight up to about 2000 and selected from the group consisting of compounds having one or more benzene nuclei and at least one phenolic OH group and compounds of hydroxynaphthalene, hydroxyindole, and hydroxyquinoline.

2. A secretin preparation as in claim 1 wherein said phenolic depot body is a compound containing up to 12 benzene nuclei at least one of which has from 1 to 3 phenolic OH groups, and wherein said benzene nuclei are condensed to form compounds of hydroxynaphthalene, hydroxyindole, or hydroxyquinoline, or are bound directly to one another, or are bound by a bridging member selected from the group consisting of hydroxyalkyl, ether, thioether, carbonamide, sulfoxide, sulfone, urethane, disulfide, ketone, phosphoric acid ester, and alkylphosphine oxide groups all having up to 8 linearly-arrayed atoms, and alkyl having up to 8 carbon atoms.

3. A secretin preparation as in claim 2 wherein said phenolic depot body includes a benzene nucleus or a bridging member, or both, which is substituted by $C_1$-$C_8$ alkyl, $C_4$-$C_8$ cycloalkyl, or by a hydroxyalkyl, alkyl sulfoxide, alkyl sulfone, phosphoric acid alkyl ester, dialkyl phosphine, or alkylphosphinic acid group wherein the alkyl groups have up to 8 carbon atoms, or by a halogen, nitro, carboxy, carbonamido, sulfonic acid, sulfonamide or phosphoric acid group.

4. A subcutaneously administrable secretin preparation as in claim 1 which additionally comprises a carrier pharmaceutically acceptable for subcutaneous administration.

5. A subcutaneously administrable secretin preparation as in claim 4 which additionally comprises a neutral, isotonic, gelatin derivative selected from the group consisting of (1) cross-linked products prepared by reacting collagen degradation products having a molecular weight from 2000 to 20000 and containing amino and guanidino groups with an amount of a diisocyanate which is less than equivalent to said amino and guanidino groups at a temperature from 0° C. to 100° C. under neutral or slightly alkaline conditions, and (2) cross-linked products as in (1) which have been degraded in aqueous solution at a temperature from 60° C. to 150° C. to fragments having a molecular weight from 10000 to 100,000.

6. A rectally administrable secretin preparation as in claim 1 which additionally comprises a carrier pharmaceutically acceptable for rectal administration.

7. A rectally administrable secretin preparation as in claim 6 wherein said phenolic depot body is 3,5-dihydroxybenzoyl-L-tyrosine.

8. A method for treating ulcers and preventing hemorrhages of the intestinal track in a patient requiring such treatment, which method comprises subcutaneously administering to said patient an effective amount of a secretin preparation as in claim 4.

9. A method for treating ulcers and preventing hemorrhages of the intestinal track in a patient requiring such treatment, which method comprises rectally administering to said patient an effective amount of a secretin preparation as in claim 6.

* * * * *